US010786925B1

(12) United States Patent
Barker

(10) Patent No.: US 10,786,925 B1
(45) Date of Patent: Sep. 29, 2020

(54) OPTICAL METHOD AND APPARATUS FOR MEASURING OBJECTS

(71) Applicant: OnSize Inc., Seattle, WA (US)

(72) Inventor: Earl M. Barker, Seattle, WA (US)

(73) Assignee: OnSize Inc., Seattle, WA (US)

( * ) Notice: Subject to any disclaimer, the term of this patent is extended or adjusted under 35 U.S.C. 154(b) by 0 days.

(21) Appl. No.: 16/797,642

(22) Filed: Feb. 21, 2020

(51) Int. Cl.
| B27B 3/18 | (2006.01) |
| B27B 31/06 | (2006.01) |
| G02B 7/00 | (2006.01) |
| B23Q 17/20 | (2006.01) |
| G01N 21/00 | (2006.01) |
| H04N 5/225 | (2006.01) |

(52) U.S. Cl.
CPC ........... *B27B 3/18* (2013.01); *B23Q 17/20* (2013.01); *B27B 31/06* (2013.01); *G01N 21/00* (2013.01); *G02B 7/003* (2013.01); *H04N 5/2254* (2013.01)

(58) Field of Classification Search
None
See application file for complete search history.

(56) References Cited

U.S. PATENT DOCUMENTS

| 3,501,683 | A | * | 3/1970 | Morecroft | G01J 3/4535 |
| | | | | | 318/687 |
| 3,552,221 | A | * | 1/1971 | Tates | F16H 35/00 |
| | | | | | 74/142 |
| 3,554,651 | A | * | 1/1971 | Ware | G01B 5/163 |
| | | | | | 356/138 |
| 5,034,259 | A | | 7/1991 | Barker | |
| 5,135,597 | A | | 8/1992 | Barker | |
| 5,680,219 | A | * | 10/1997 | Rydningen | G01B 11/024 |
| | | | | | 356/635 |
| 5,699,161 | A | * | 12/1997 | Woodworth | G01B 11/00 |
| | | | | | 356/628 |
| 5,742,068 | A | * | 4/1998 | Dybdahl | G01S 17/08 |
| | | | | | 250/559.19 |
| 6,100,986 | A | * | 8/2000 | Rydningen | G01B 11/022 |
| | | | | | 356/630 |
| 6,175,429 | B1 | * | 1/2001 | Nagaharu | G02B 7/04 |
| | | | | | 358/475 |
| 6,324,016 | B1 | * | 11/2001 | Luster | G02B 13/22 |
| | | | | | 359/364 |
| 6,952,231 | B1 | * | 10/2005 | Paavola | G02B 13/22 |
| | | | | | 348/142 |
| 7,853,349 | B2 | | 12/2010 | Barker | |

(Continued)

*Primary Examiner* — Shawn Decenzo
*Assistant Examiner* — Jarreas C Underwood
(74) *Attorney, Agent, or Firm* — Cozen O'Connor

(57) ABSTRACT

A sawing inspection system to measure dimensions of a cant that has been cut into pieces is disclosed. The system includes a housing having a window, an image sensor, a first mirror, and a second mirror. The first mirror includes a concave parabolic reflective surface and a focal point, and the second mirror includes a flat, reflective surface. The focal point is where parallel rays of light that enter the housing through the window and reflect off of the concave parabolic reflective surface intersect. The second mirror is positioned to reflect toward the focal point the parallel rays of light reflected by the first mirror. The image sensor is located at the focal point. At least one of the first mirror, the second mirror, and the image sensor is movable relative to the others to remove parallax error from the measurement of the pieces of the cant.

26 Claims, 10 Drawing Sheets

(56) References Cited

U.S. PATENT DOCUMENTS

| | | |
|---|---|---|
| 7,886,642 B2 | 2/2011 | Barker |
| 7,914,175 B2 | 3/2011 | Barker et al. |
| 7,993,019 B2 | 8/2011 | Barker et al. |
| 8,229,803 B2 | 7/2012 | Barker |
| 8,346,631 B2 | 1/2013 | Barker |
| 8,370,222 B2 | 2/2013 | Barker |
| 9,505,072 B2 | 11/2016 | Barker |
| 9,827,643 B2 | 11/2017 | Barker |
| 2004/0125417 A1* | 7/2004 | Chen .................... H04N 1/1052 358/474 |
| 2006/0053990 A1 | 3/2006 | Barker |
| 2009/0076741 A1 | 3/2009 | Barker |
| 2014/0014634 A1* | 1/2014 | Liu ...................... B23K 26/361 219/121.68 |
| 2014/0238546 A1 | 8/2014 | Barker |
| 2014/0251499 A1 | 9/2014 | Barker |

* cited by examiner

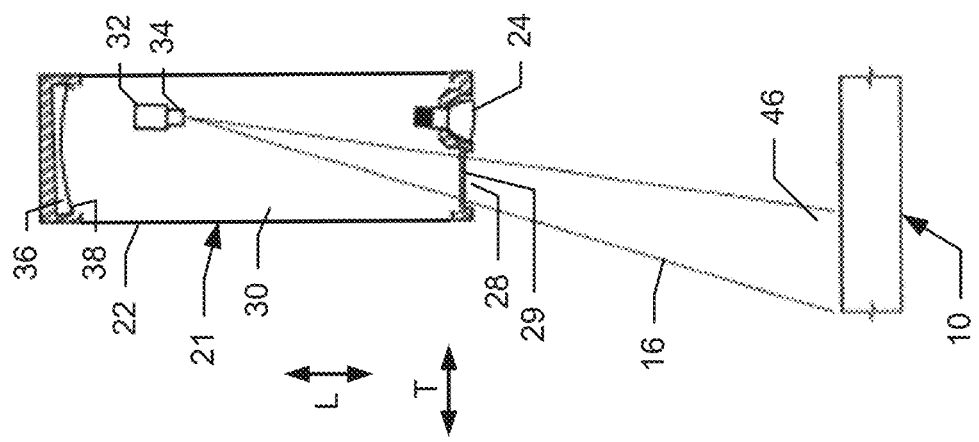
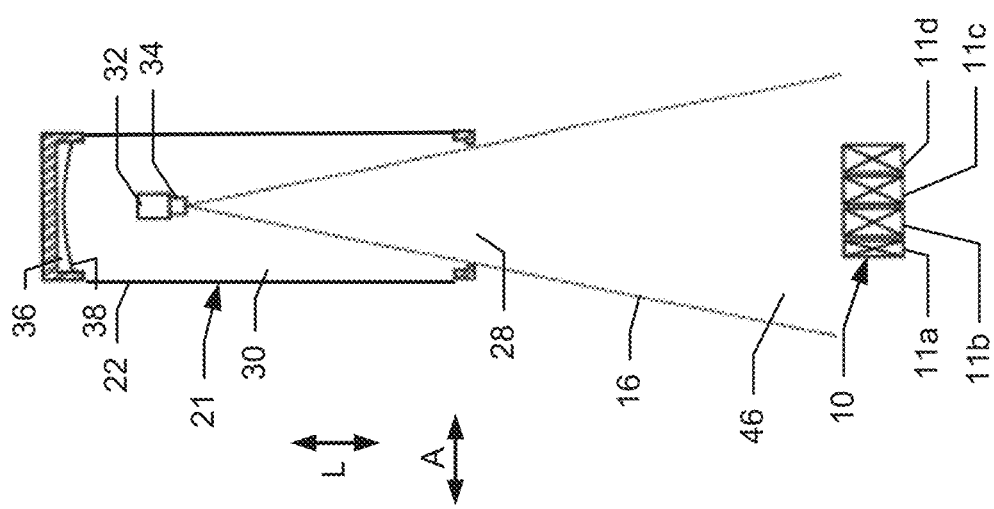

OPTICAL METHOD AND APPARATUS FOR MEASURING OBJECTS

BACKGROUND

Technical Field

The present disclosure pertains to the field of optical measurement techniques, and more particularly to optical methods and apparatuses for measuring objects, such as wooden logs or cants, to monitor performance of machinery used to cut said wooden logs or cants into dimensional lumber.

Description of the Related Art

Many products are made primarily from wood. Wood is used as a structural building material, as a packaging material, and as a material in making finished products. Typically wood is harvested during a first operation, which includes cutting down trees and converting them into logs. The logs may then be processed, for example at a sawmill, to convert the logs first into cants and then into dimensional lumber.

The sawmill industry has become largely automated. Full length tree trunks are delivered to sawmills, where they are automatically debarked, scanned and cut into log segments based on their scanned geometry. These log segments are then typically processed at a number of automated stations, depending on the sawmill and the type of wood. These processing stations produce lumber from each log segment, often without any human intervention.

One of the first processing stations in many sawmills is the primary breakdown machine, which processes log segments to produce cants and sideboards. The primary breakdown machine typically includes chip heads for removing slabs as well as one or more band saws for removing sideboards from the log segments. Each log segment may be scanned prior to processing at the primary breakdown machine, and a primary breakdown computer optimizer may then determine an optimal mix of lumber that can be obtained from that log segment based on the scanned geometry. The computer optimizer may then rotate the log segment and control the relative position of the chip heads and band saws to achieve that optimal mix of lumber.

Downstream from the primary breakdown machine, cants may be further processed at a gangsaw to produce boards. Gangsaws typically include a number of parallel, circular saw blades located at precise intervals within a sawbox. Cants may be transported in a straight line through the gangsaw using feed rolls on the upstream and downstream sides of the sawbox. Alternatively, the cants may be curve sawed. The sawbox may be moved during the cutting to produce a curved sawing path. In many sawmills, a cant scanner scans the incoming cants prior to processing by the gangsaw. A gangsaw computer optimizer then determines optimal locations for the chip heads and saw blades based on the scanned geometry of each cant.

Boards sawn by the gangsaw, as well as sideboards from the primary breakdown machine, may then be processed by an edger. The edger typically includes one or more saw blades for sawing along the length of the boards to achieve a chosen width. After edging, the boards are transported to a trimmer, where the boards can be trimmed to a final length. Both the edger and the trimmer may also have corresponding scanning systems and computer optimizers to determine how best to saw each piece of lumber.

At each processing station, an optimizer system makes determinations regarding the optimal way to saw each piece to maximize the value and volume of lumber produced from the raw logs. Dimensional lumber includes wood lumber that is sawn to standardized sizes having nominal depth and width sizes (e.g., "2×4" boards, "2×6" boards, "4×4" boards), and of a variety of lengths (e.g., 6', 8', 10', 12', 14', 16', 18', 20', 22' and 24'). Notably, the actual dimensions of any given finished (e.g., dried and planed) piece of lumber are at least for softwoods (e.g., Douglas Fir, Pine) typically slightly smaller than nominal dimensions of that of piece of lumber. For example, a typical finished "2×4" board may have actual dimensions as small as 1½"×3½".

The dimensions of a board undergo multiple reductions throughout the process of turning a log into dimensional lumber. The log may be processed into a cant by cutting off one or more sides of the log to form one or more flat surfaces. The cant may then undergo one or more sawing operations to form boards from the cant. Each of the boards has a target size, which may be referred to as rough, green dimensions.

For example, a "2×4" board may have a target size of 1.68"×3.72". As the board is further processed, for example by drying and planing, the board will reduce further in size. It is important that the board's final dimensions do not decrease below the minimum acceptable value, for example 1½"×3½" for a "2×4", or the board may be rejected for sale due to quality control issues. Producing a finished board with values as close to the minimum acceptable values without going below the minimum acceptable values requires precision throughout the process.

If some portion of the sawing system is not performing properly, the size of the pieces could be out of tolerance, causing the sawmill to suffer additional losses until the problems are found and fixed. Even slight defects in sawing can significantly, adversely affect that value of lumber produced from a log or cant. For example, a gang of nominally parallel saw blades may not actually be parallel or defects may exist in one or more of the saw blades resulting in boards being sawn that are either too thick or too thin, that is boards that exceed a nominal thickness by some specified tolerance or that are below the nominal thickness by some specified tolerance. The loss in value in lumber produced over a shift in a lumber mill due to an out of tolerance condition can be substantial, particularly given the relatively low margins involved.

Thus, modern sawmills lack an effective way to determine if the processing stations are indeed functioning correctly and realizing optimal value from the raw resources. Consequently, there is a need for improvement.

BRIEF SUMMARY

When imaging a log or cant, the distance from the log or cant to the lens varies as a result of the three-dimensional shape of the object. Areas of the log that are located at a greater distance from an image sensor (e.g., digital camera), such as the lateral portions, are seen as smaller in size than the central portion. This distortion is due to parallax error. Removal of sources of parallax error from an automated imaging process may result in improved lumber yield from a given log or cant. Additionally, a system that is adjustable such that the system can be integrated in various environments with different operating parameters may result in lower costs for the manufacturing and installation of such systems.

The present disclosure provides one or more solutions to these and other problems.

According to one aspect of the disclosure, an image capture apparatus, includes a housing having a window, and a first mirror located in the housing. The first mirror having a concave parabolic reflective surface, and the first mirror having a focal point at which parallel rays of light that enter the housing through the window and reflect off of the concave parabolic reflective surface intersect. The image capture apparatus further includes a second mirror located in the housing, the second mirror having a flat reflective surface, and the second mirror positioned and oriented in the housing to reflect toward the focal point the parallel rays of light reflected by the first mirror. The image capture apparatus includes at least one image sensor located in the housing at the focal point.

The second mirror is spaced from the first mirror by a first distance measured along a direction parallel to the parallel rays of light. The at least one image sensor is spaced from the second mirror by a second distance measured along the direction parallel to the parallel rays of light. At least one of the first mirror, the second mirror, and the at least one image sensor is movable relative to the others of the first mirror, the second mirror, and the at least one image sensor such that at least one of the first distance and the second distance is adjustable.

According to another aspect of the disclosure, a sawing inspection system includes a plurality of image capture apparatuses coupled together.

According to yet another aspect of the disclosure, a method of manufacturing a sawing inspection system includes providing a housing having a window, and locating a first mirror in the housing. The first mirror includes a concave parabolic reflective surface, and the first mirror has a focal point at which parallel rays of light that enter the housing through the window and reflect off of the concave parabolic reflective surface intersect. The method further includes locating a second mirror in the housing such that a flat reflective surface of the second mirror is positioned and oriented to reflect toward the focal point the parallel rays of light reflected by the first mirror. The second mirror is spaced from the first mirror by a first distance that is measured along a direction parallel to the parallel rays of light.

The method further includes locating at least one image sensor in the housing such that the at least one image sensor is spaced from the first mirror by a second distance that is measured along the direction parallel to the parallel rays of light, and adjusting at least one of the first distance and the second distance to position the at least one image sensor at the focal point. When the at least one image sensor is at the focal point the at least one image sensor has a direct line of sight through the window of the housing.

According to yet another aspect of the disclosure, a method of measuring at least one dimension of a cant that has been sawn into at least one board, includes activating a source of illumination to produce light which reflects off of the cant, and positioning an image capture apparatus such that parallel rays of light from the light that has reflected off of the cant passes through a window of a housing of the image capture apparatus, then reflects off of a concave parabolic reflective surface of a first mirror of the image capture apparatus, and then is received by an image sensor of the image capture apparatus positioned at a focal point of the first mirror at which the parallel rays of light intersect.

The method further includes simultaneously capturing a first image of the object and a second image of the object, the first image generated based on the parallel rays of light that reflected off of the first mirror to the image sensor, and the second image based on light reflected off of the cant, through the window, and directly to the image sensor without reflecting off the first mirror.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings.

FIG. 6 is another top, plan, schematic view of the image capture apparatus illustrated in FIG. 3.

FIG. 7 is a side, elevation, schematic view of the image capture apparatus illustrated in FIG. 6.

DETAILED DESCRIPTION

Figure 1:
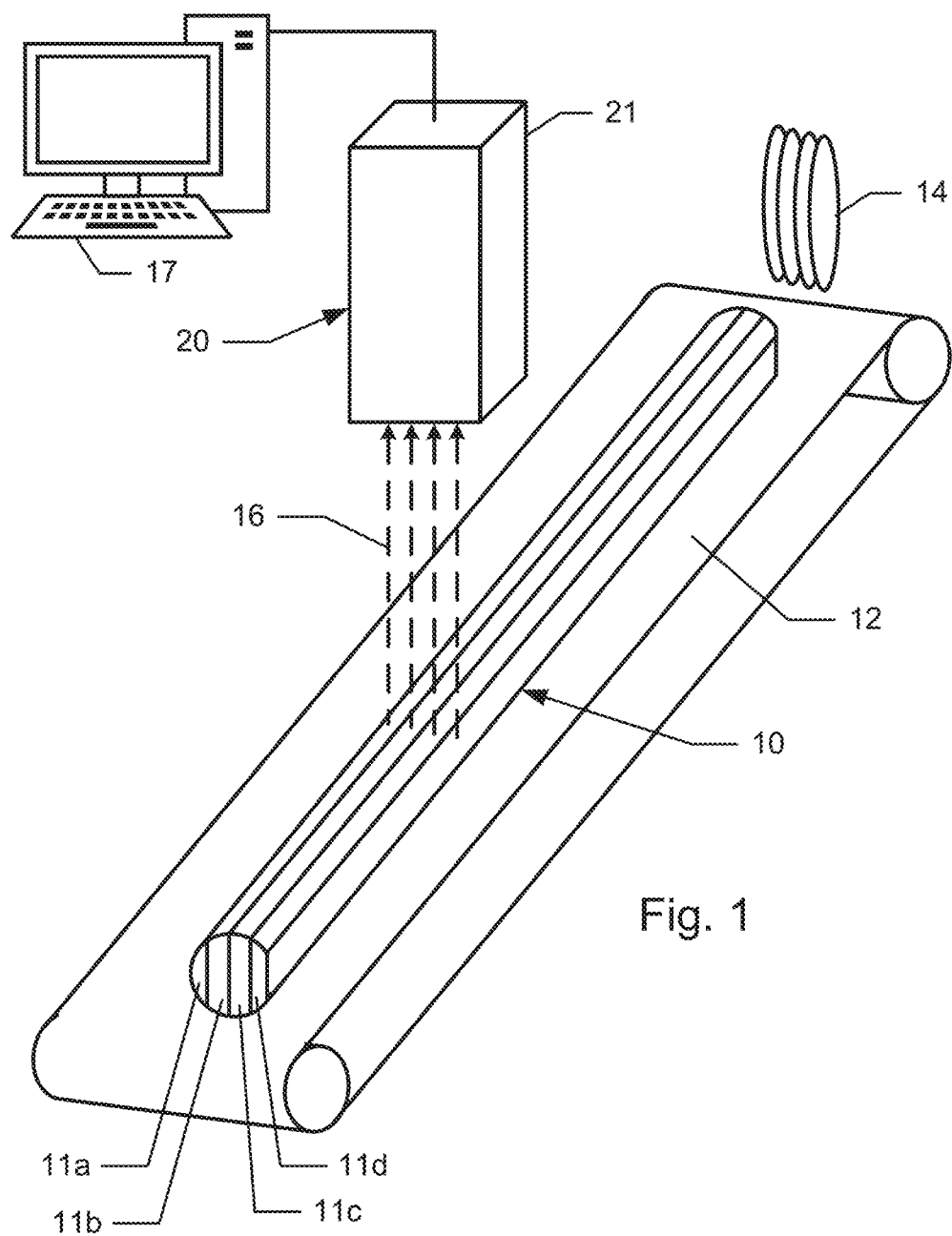
FIG. 1 is an isometric view of an inspection system, according to one embodiment.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with the disclosed subject matter have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment," "an embodiment," or "an aspect of the disclosure" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its broadest sense, that is as meaning "and/or" unless the content clearly dictates otherwise.

Reference herein to two elements "facing" or "facing toward" each other indicates that a straight line can be drawn from one of the elements to the other of the elements without contacting an intervening solid structure. Reference herein to two elements being "directly coupled" indicates that the two elements physically touch with no intervening structure between.

Reference herein to a first object having a direct line of sight to a second object indicates that there is a straight, uninterrupted optical path, that is not reliant on reflection from one or more mirrors, from the first object to the second object. Reference herein to a first object having an indirect line of sight to a second object indicates that there is a non-straight optical path, for example reflecting off one or more mirrors, from the first object to the second object. Reference herein to a first object having a direct line of sight to a second object does not preclude the first object from also having an indirect line of sight to the second object, and vice versa.

The term "aligned" as used herein in reference to two elements along a direction means a straight line that passes through one of the elements and that is parallel to the direction will also pass through the other of the two elements. The term "between" as used herein in reference to a first element being between a second element and a third element with respect to a direction means that the first element is closer to the second element as measured along the direction than the third element is to the second element as measured along the direction. The term "between" includes, but does not require that the first, second, and third elements be aligned along the direction.

Aspects of the disclosure will now be described in detail with reference to the drawings, wherein like reference numbers refer to like elements throughout, unless specified otherwise. Certain terminology is used in the following description for convenience only and is not limiting. The term "plurality," as used herein, means more than one. The terms "a portion" and "at least a portion" of a structure include the entirety of the structure.

The headings and Abstract of the Disclosure provided herein are for convenience only and do not interpret the scope or meaning of the embodiments.

Referring to FIG. 1, an object 10 moves, for example along a conveyor belt 12, relative to an inspection system 20, for example a sawing inspection system. The object 10, according to one embodiment, may be a log or a cant. The log or cant may be either uncut or the log may have already been processed by one or more cutting or sawing operations to produce a cant. For example, as shown in the illustrated embodiment, the object 10 has been cut into a number of pieces 11a-11d by one or more saw blades 14.

The inspection system 20 includes an image capture apparatus 21 that captures an image of the object 10 to determine dimensions of the object 10. The inspection system 20 may include at least one processor 17, for example a computer, communicatively coupled to the image capture apparatus 21. The determined dimensions may also be used for quality control purposes, for example ensuring that the pieces 11a-11d are within acceptable tolerances for the desired dimensional lumber. Additionally, the determined dimensions may provide information related to maintenance of the saw mill, for example whether the saw blades 14 are properly sharpened and/or notifying an operator that the control systems responsible for movement of the saw blades 14 are in need of calibration.

According to one embodiment, the object 10 is a cant, which has been produced from a log by processing the log to remove bark and one or more side boards. The cant may have been scanned to determine the optimal dimensional lumber to be produced from the cant based on the cant's dimensions. The saw blades 14, which may be part of a gangsaw, are positioned so as to form multiple cuts in the cant, thereby producing the pieces 11a-11d each with a thickness that corresponds to the target size for the optimal dimensional lumber.

Figure 2:
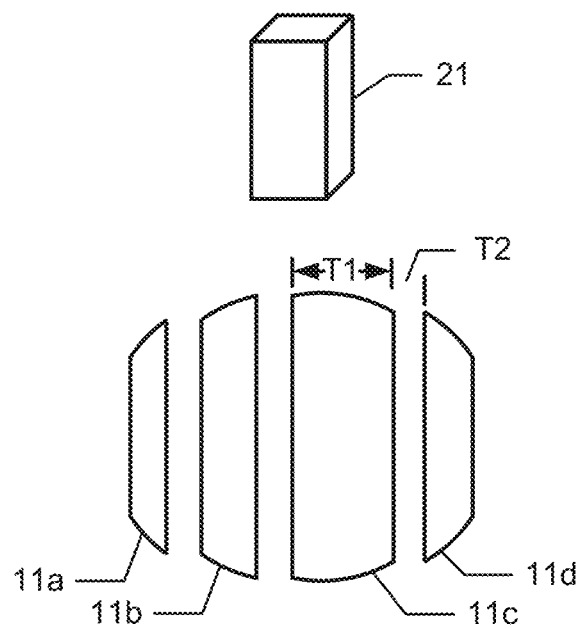
FIG. 2 is a front, elevation view of an image capture apparatus of the inspection system and pieces of an object being imaged by the image capture apparatus, according to one embodiment.

Referring to FIGS. 1 and 2, the pieces 11a-11d of the cant may then pass through a field of view of the image capture apparatus 21, which measures dimensions of the cant. For example, the image capture apparatus 21 may measure the thickness T1 of one or more of the pieces 11a-11d, the thickness T2 of one or more of the cuts, or both. The inspection system 20 may then compare the measured dimensions with predetermined acceptable dimensions for the optimal dimensional lumber and identify each of the pieces 11a-11d as being acceptable (within tolerances of the predetermined acceptable dimensions) or being unacceptable (outside tolerances of the predetermined acceptable dimensions).

The acceptable/unacceptable identifications for each of the pieces 11a-11d of each cant may then be stored, compiled, displayed, or any combination thereof. The compiled identifications may be used to pinpoint problems within a sawmill. For example, if one of the pieces 11a-11d of numerous cants that is associated with a particular one of the saw blades 14 is identified as unacceptable, it may indicate that the particular saw blade is in need of maintenance (e.g., sharpening, replacement).

The determined dimensions may also be used to optimize a future cutting operation performed on the object. According to one embodiment, the optimization may prioritize efficient use of the available material within the object, for example such that waste material within the object is minimized. According to one embodiment, the optimization may prioritize certain dimensions of lumber, for example 2"×8" boards may be prioritized over 2"×4" boards.

Figure 3:
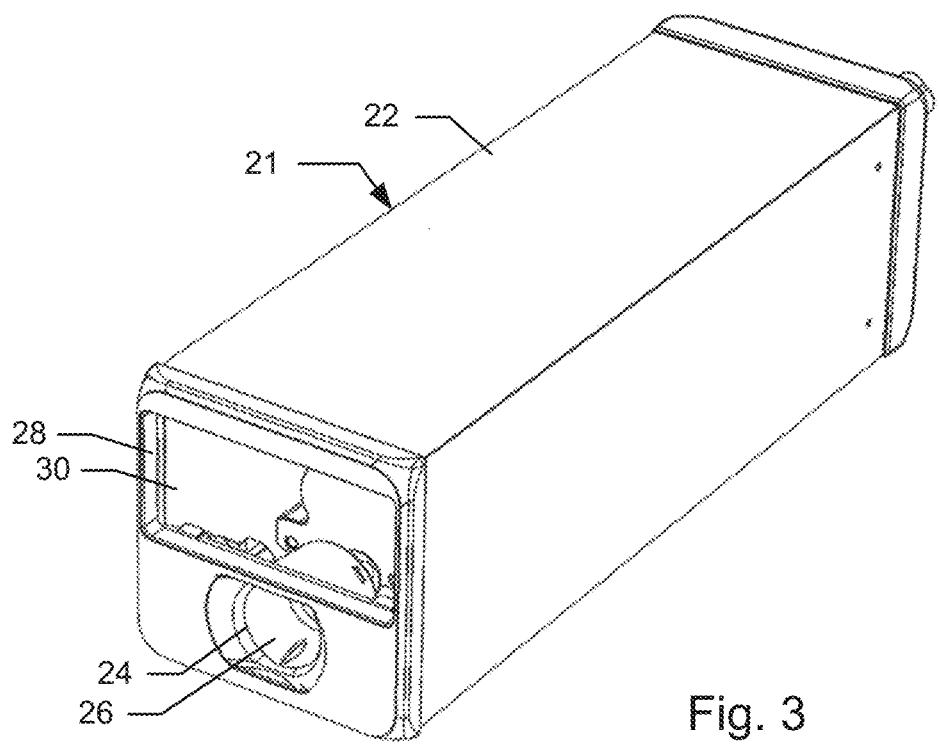
FIG. 3 is an isometric view of the image capture apparatus illustrated in FIG. 2, according to one embodiment.

Referring to FIG. 3, the inspection system 20 may include a housing 22, which at least partially encloses one or more internal components of the inspection system 20. The inspection system 20 may include a radiation source 24, for example positioned within the housing 22. According to one embodiment, the radiation source 24 may be a flood illumination source, for example a light source 26, and the light source 26 may be positioned so as to illuminate the object 10 as the object 10 moves relative to the inspection system 20. The light source 26 may include at least one light emitter diode (LED). According to one embodiment, the radiation source 24 may be provided by an external component that is remote from the housing 22.

Referring to FIGS. 1 to 3, the housing 22 may include a window 28 through which the light 16, for example light generated from the light source 24, that has reflected from the object 10 enters the housing 22 to interact with the internal components of the inspection system 20. The window 28 may include an opening or void with an outer perimeter established by the housing 22. The window 28 may include a cover 29 (shown in FIG. 7), for example window glass, which allows passage of the reflected light 16 and blocks entry of particles (such as saw dust) into an interior 30 of the housing 22 to prevent said particles from negatively impacting the performance of the internal components of the inspection system 20.

Referring to FIGS. 4 to 7, the inspection system 20 may include an image sensor 32. The image sensor 32 may be positioned within the interior 30 of the housing 22. The image sensor 32, according to one embodiment, may include a camera 34 that captures one or more images of the object 10. The camera 34 may then transmit data, such as the captured image(s), to the processor 17 (shown in FIG. 1) for example a computer, which receives and then processes the data and calculates results, for example dimensions of the object 10.

The inspection system 20 may include a first mirror 36 located within the housing 22. The first mirror 36 may include a concave reflective surface 38. According to one embodiment, the concave reflective surface has a parabolic shape with a focal point 39 at which parallel rays 19 of the light 16 that enter the housing 22 through the window 28 and reflect off of the concave parabolic reflective surface 38 intersect.

According to one implementation, the concave parabolic reflective surface 38 has a shape that is at part of a circular paraboloid, that is, the concave parabolic reflective surface 38 is generated by a parabola revolving around an optical axis 41 of the first mirror 36.

The inspection system 20 may include a second mirror 40 located within the housing 22. The second mirror 40 may include a reflective surface 42, for example a flat planar reflective surface. The first mirror 36 and the second mirror 40 may be supported by the housing 22 such that at least one of the first mirror 36 and the second mirror 40 is movable relative to the other of the first mirror 36 and the second mirror 40. For example, the second mirror 40 may be movable along a first direction L relative to the first mirror 36, the first mirror 36 may be movable along the first direction L relative to the second mirror 40, or both the first mirror 36 and the second mirror 40 may be movable along the first direction L relative to the housing 22.

As shown in the illustrated embodiment, a first distance D1 is measured from the first mirror 36 to the second mirror 40 along the first direction L, and at least one of the first mirror 36 and the second mirror 40 is movable along the first direction L. The first distance D1 may be measured from an optical center of the concave reflective surface 38 to the reflective surface 42, for example an optical center of the reflective surface 42.

The first mirror 36 may be positioned and oriented within the housing 22 such that the parallel rays 19 of the light 16 generated from the light source 24 that has reflected from the object 10 and entered the housing 22 through the window 28, reflects off of the concave reflective surface 38, then reflects off of the reflective surface 42, and then is received by the image sensor 32.

As shown, the first mirror 36 may be positioned farther from the window 28 than the second mirror 40 is from the window 28 as measured along the first direction L. Alternatively, the first mirror 36 may be positioned closer to the window 28 than the first mirror 40 is from the window 28 as measured along the first direction L. According to one embodiment, the image sensor 32 may be positioned between the first mirror 36 and the second mirror 40 with respect to the first direction L. The image sensor 32 may be positioned centrally within the housing 22 with respect to a second direction A, which is perpendicular to the first direction L. The image sensor 32 may be positioned off-center within the housing 22 with respect to a third direction T, which is perpendicular to both the first direction L and the second direction A.

The shape of the concave parabolic reflective surface 38 may, as shown, extend radially from the optical axis 41. For example the shape of the concave parabolic reflective surface 38 may be parabolic along more than one direction, for example along both the second direction A and the third direction T. Alternatively, the concave parabolic reflective surface 38 may be parabolic along only a single direction, such that the concave parabolic reflective surface 38 is only parabolic along a single line. The concave parabolic reflective surface 38 being parabolic along more than one direction may provide additional functionality of the image capture apparatus 21, as will be explained in further detail below.

As shown in the illustrated embodiment, a second distance D2 may be measured from the second mirror 40 to the image sensor 32 along the first direction L. According to one implementation at least one of the second mirror 36 and the image sensor 32 is movable along the first direction L. Adjustment of the second distance D2 may allow the image sensor 32 to be positioned accurately at the focal point 39, thus enabling removal of parallax error from images of the object 10 captured by the image capture apparatus 21. Thus, according to one implementation, the first mirror 38, the second mirror 40, and the first image sensor 32 are all positioned relative to one another such that the first distance D1 plus the second distance D2 equals a focal length of the first mirror 36, and the image sensor 32 is positioned at the focal point 39.

Removal of parallax error enables flexibility in the positioning of the image capture apparatus 21 relative to the object 10 along the first direction L. The image capture apparatus 21 may be positioned relative to the object 10 such that a third distance D3 may be measured from the window to the object along the first direction L. Accurate removal of the parallax error allows the third distance D3 to be chosen according to the resources available at the measurement location, for example the sawmill, as the measurement of the dimensions of the object 10 will remain constant even as the third distance D3 changes.

The first mirror 36 may be positioned and oriented within the housing 22 such that the parallel rays 19 of the light 16 generated from the light source 24 that have reflected from the object 10 and entered the housing 22 through the window 28, reflect off of the concave reflective surface 38, then reflect off of the reflective surface 42, and then are received by the image sensor 32.

According to one embodiment, the first mirror 36 may be supported within the housing 22 such that the optical axis 41 of the first mirror 36 is non-parallel with the first direction L. For example, the optical axis 41 may be angularly offset by between 1 degree and 4 degrees with respect to an axis parallel to the first direction L. According to one embodiment, the second mirror 40 may be supported within the housing 22 such that the optical axis 41 of the second mirror 40 is non-parallel with the first direction L. The first mirror 36 and the second mirror 40 may be supported within the housing 22 such that the optical axis of the first mirror is non-parallel with respect to the optical axis of the second mirror 40.

According to one implementation, the image capture apparatus 21 may include the first mirror 36 and may be devoid of the second mirror 40. Thus, the image sensor 32 may face the concave reflective surface 38 and may be positioned such that the parallel rays 19 of the light 16 generated from the light source 24 that have reflected from the object 10 and entered the housing 22 through the window 28, reflect off of the concave reflective surface 38, and then are received by the image sensor 32. Inclusion of the second mirror 40 enables a more compact construction of the image capture apparatus 21 which may result in easier manufacture, installation, and maintenance compared to the implementation of the image capture apparatus 21 that is devoid of the second mirror 40.

According to one embodiment, the image sensor 32 may be positioned within the housing 22 such that the image sensor 32 has a first field of view 44 based on indirect line of sight (reflecting off at least one of the first mirror 36 and the second mirror 40), and a second field of view 46 based on direct line of sight (i.e. a straight, uninterrupted path, for example a path that is not reliant on reflection from one or more mirrors within the housing 22) to the object 10. As shown, the second field of view 46 may be wider than the first field of view 44, as the second field of view 46 is not reliant on the parallel rays 19 of the light 16. Thus, the second field of view 46 may provide additional information about areas on or around the object 10 proximate edges of the first field of view 44.

Figure 5:
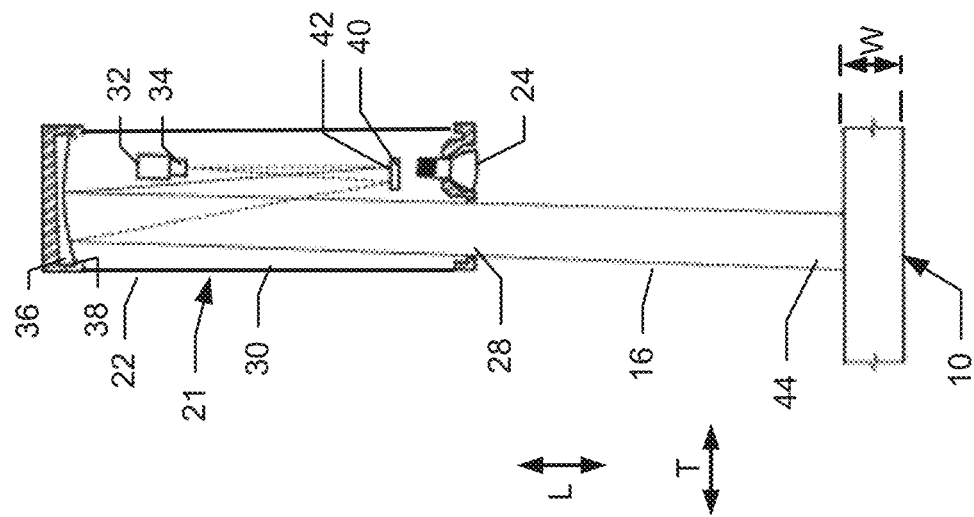
FIG. 5 a side, elevation, schematic view of the image capture apparatus illustrated in FIG. 4.
Figure 4:
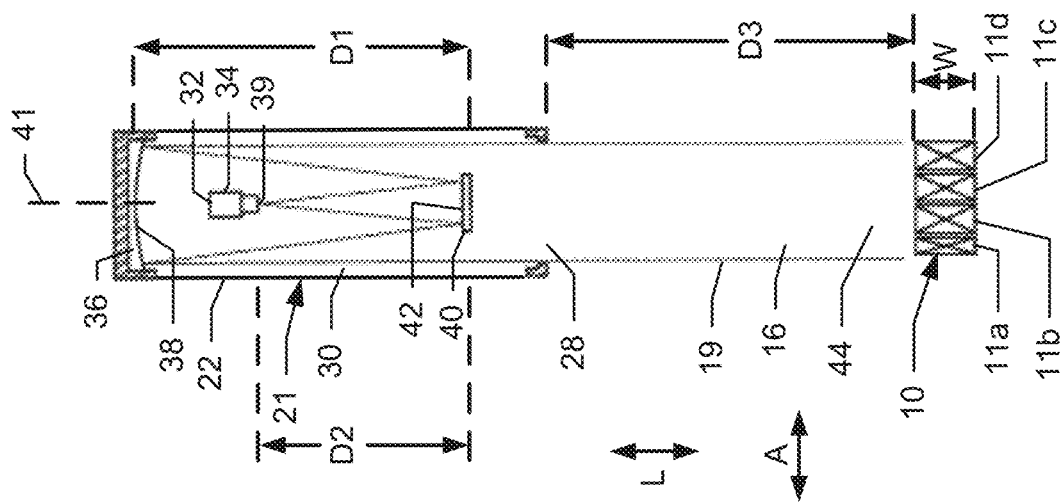
FIG. 4 is a top, plan, schematic view of the image capture apparatus illustrated in FIG. 3, according to one embodiment.

Thus, the inspection system 20 may be constructed and positioned such that the light 16 from the light source 24 has at least two paths to the image sensor 32. The at least two paths may include a first path from the light source 24, reflecting off the object 10, through the window 28, reflecting off the concave reflective surface 38, reflecting off the reflective surface 42, and into the image sensor 32 (as shown in FIGS. 4 and 5), and a second path from the light source 24, reflecting off the object 10, through the window 28, and directly into the image sensor 32 (as shown in FIGS. 6 and 7).

Figure 8:
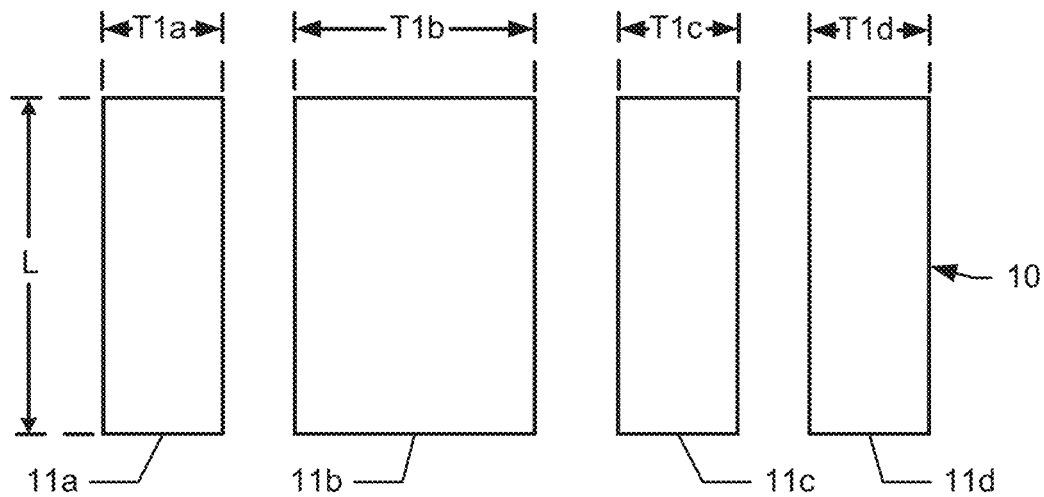
FIG. 8 is a schematic view of a parallax corrected image, of a portion of an object according to one embodiment.
Figure 9:
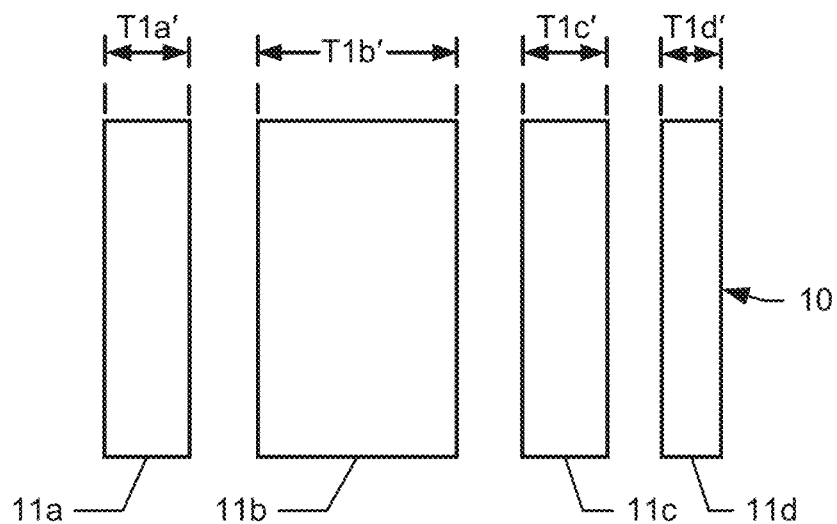
FIG. 9 is a schematic view of a non-parallax corrected image of the portion of the object illustrated in FIG. 8.

Referring to FIGS. 4 to 9, adjustment of at least one of the first distance D1 and the second distance D2 to position the image sensor 32 at the focal point 39, thereby removing parallax error from the image captured by the image sensor 32 may enable more accurate measurement of the pieces 11a-11d of the object 10. In a non-parallax corrected image, different objects, or portions of objects, appear distorted based on their different distances to the image sensor 32. Thus, when in reality the thickness T1a of the first piece 11a may be half the size of the thickness T1b of the second piece 11b (as shown in FIG. 8), in a non-parallax corrected image the first piece 11a may appear to have a thickness T1a' that is less than half the thickness T1b' of the second piece 11b (as shown in FIG. 9).

Similarly, when in reality the thickness T1c of the third piece 11c may be equal to the size of the thickness T1d of the fourth piece 11d (as shown in FIG. 8), in a non-parallax corrected image the third piece 11c may appear to have a thickness T1c' that is greater than the thickness T1d' of the fourth piece 11d (as shown in FIG. 9). This difference may be due to the fourth piece 11d being farther from the image sensor 32 than the third piece 11c. Thus, measurements based on a non-parallax corrected image may be less accurate than measurements based on a parallax corrected image.

Additionally, positioning of the image sensor 32 such that both the first path and the second path are provided may allow comparison of two different images of the same portion of the object 10, for example comparison of a parallax corrected image (from the first path, as shown in FIG. 8) with a non-parallax corrected image (from the second path, as shown in FIG. 9). Comparison of the measurements from both the parallax corrected image and the non-parallax corrected image may allow additional dimensions of the pieces 11a-11d of the object 10 to be calculated.

For example, the difference in measurements from the parallax corrected image and the non-parallax corrected image (for example the difference between the thickness T1a and the thickness T1a') may result in a ratio, which may be used (in conjunction with other known/calculable values, such as one or more of a distance of the image capture apparatus 21 to the top of the object 10, a distance of the image capture apparatus 21 to the bottom of the object 10) to calculate a width W of the respective pieces 11a-11d of the object 10.

As described above, the concave parabolic reflective surface 38 being parabolic along more than one direction may provide additional functionality of the image capture apparatus 21. When the concave parabolic reflective surface 38 includes a concave parabolic area, it enables the image sensor 32 to capture a parallax corrected image of an area of the object 10, as opposed to capturing a parallax corrected image of a line of the object 10. Capturing a parallax corrected image of an area of the object 10 enables additional error reduction and quality controls to be implemented into the sawing inspection system 20.

According to one implementation, the sawing inspection system 20, for example the processor 17, may conduct a summation of values within the captured image. Edges of objects, such as a sawn edge of a cant, are often rough (especially as magnification increases toward a microscopic level). Additionally, debris, such as dirt or saw dust, may obscure a portion of the parallel rays 19 of the light 16 as they travel toward the window 28.

To correct for these potential sources of error, the processor may analyze a plurality of data points, for example pixels, along a length L of the image. Each of the pixels along a line running parallel to the length L may be assigned a "brightness value" for example from 1 (equating to a dark pixel) to 255 (equating to a bright pixel). Summing all of the brightness values along the length for a line will compensate for errors. For example if 100 pixels along the length L are summed and 90 of the pixels have a brightness value of 255, while 10 of the pixels have a brightness of 1, the processor 17 may determine that the line of pixels is "bright" and produce a result that indicates that the object 10 is present along the line (as opposed to a relatively dark cut being present along the line).

Figure 10:
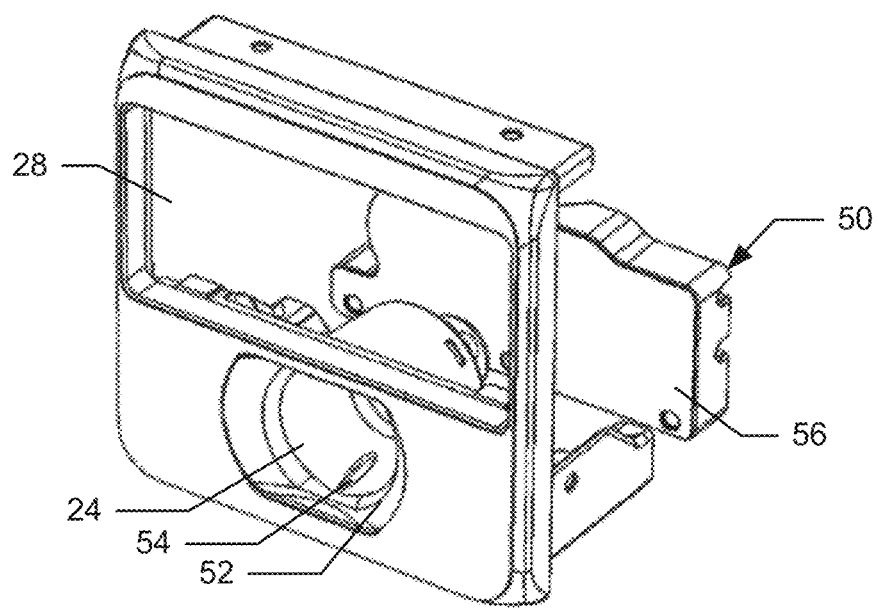
FIG. 10 is an isometric view of a light source, a first carriage, and a window of the image capture apparatus illustrated in FIG. 3.
Figure 11:
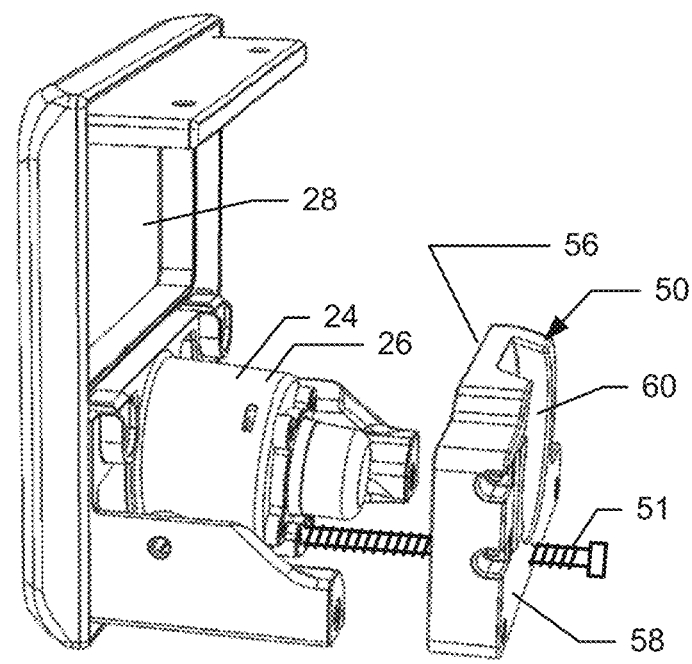
FIG. 11 is another isometric view of the light source, the first carriage, and the window illustrated in FIG. 10.
Figure 12:
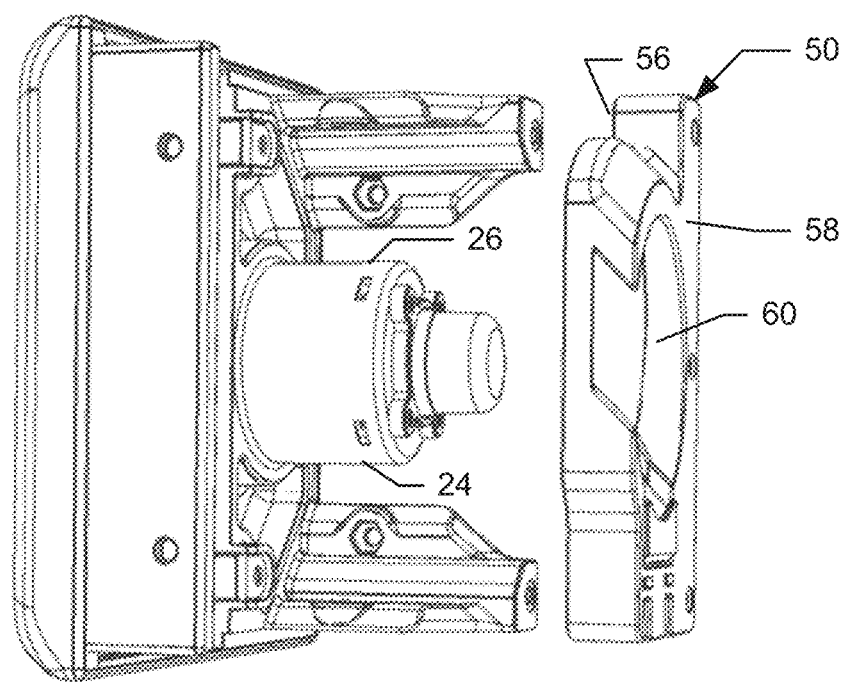
FIG. 12 is another isometric view of the light source, the first carriage, and the window illustrated in FIG. 10.

Referring to FIGS. 10 to 12, the inspection system 20 may include a first carriage 50 that carries the second mirror 40. The first carriage 50 may be translatable with respect to the housing 22 and internal components of the inspection system 20 positioned within the housing 22. According to one embodiment, the first carriage 50 is translatable so as to adjust the first distance D1 between the first mirror 36 and the second mirror 40. Alternatively, the first carriage 50 may be fixed in place with respect to the housing 22 and internal components of the inspection system 20 positioned within the housing 22.

According to one embodiment, the inspection system 20 includes a threaded fastener 51 that threadedly engages the first 50 carriage and is rotatable to translate the first carriage 50 along the first direction L, thereby adjusting the first distance D1 between the first mirror 36 and the second mirror 40. The threaded fastener 51 may include a thread pitch sized such that each one quarter turn of the threaded fastener 51 adjusts the first distance D1 by ten thousandths of an inch (0.010"). Such fine adjustments enable precise removal of the parallax error as described in detail above. It will be appreciated by those of skill in the art that adjustment of the first distance D1 may be accomplished with alternate components, for example a track and follower, a motor, etc.

As shown in the illustrated embodiment, a portion of the housing 22 carries the light source 24. The light source 24 may include a bulb (not shown) and a bulb housing 52 that partially encloses the bulb so as to direct the light 16 generated by the light source 24 toward the object 10. The bulb housing 52 may include an access 54 to an actuator, such as the threaded fastener 51, which controls movement of the first carriage 50. The access 54 may provide a path for insertion of an actuator through the housing 22 to engage with the threaded fastener 51 and adjust the first distance D1. The access 54 may be positioned such that when the bulb is positioned within the bulb housing 52, the access 54 is blocked, for example by the bulb.

This configuration enables access to the actuator during manufacture and/or installation of the inspection system 20, while preventing access to the actuator during operation of the inspection system 20. Thus, the first distance D1 may be adjusted during installation and calibration, for example by a manufacturer of the inspection system 20, while preventing adjustment of the first distance D1 during operation of the inspection system 20 by an operator of a sawmill. It will be appreciated by those of skill in the art that the inspection system 20 may include an actuator in an alternate position, for example accessible only from the interior 30 of the housing 22 when at least a portion of the housing 22 is removed, or from an exterior of the housing 22 such that the actuator is accessible during operation of the inspection system 20.

According to one embodiment, the first carriage 50 has a front face 56 that faces the window 28 and a back face 58 opposed across a thickness of the first carriage 50 from the front face 56. The back face 58 may have a recess 60 that is sized to receive the first mirror 36 such that the reflective surface 42 faces away from the window 28.

Figure 13:
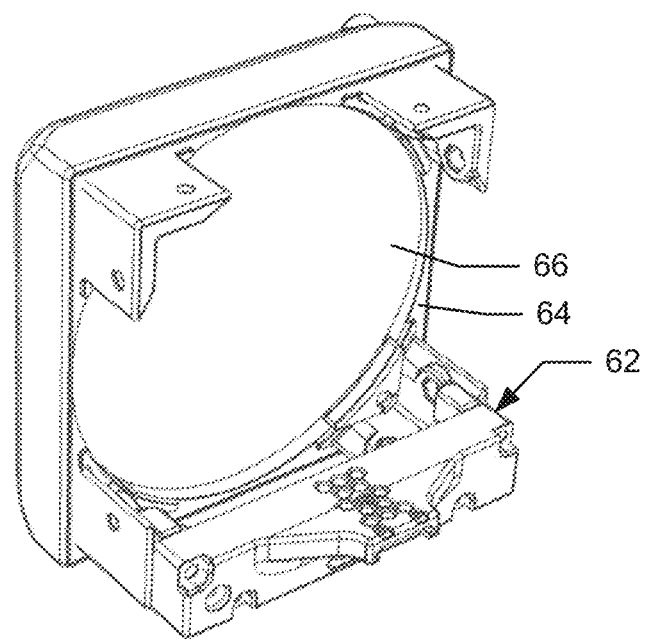
FIG. 13 is an isometric view of a second carriage of the image capture apparatus illustrated in FIG. 3.
Figure 14:
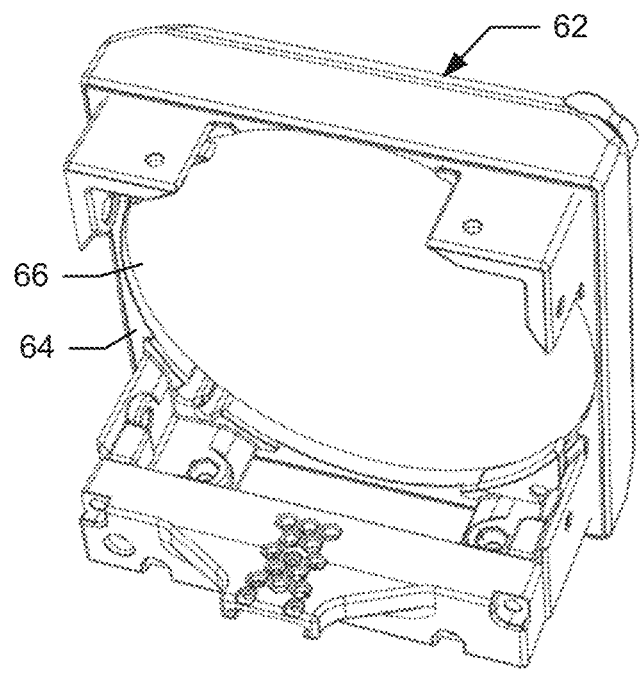
FIG. 14 is another isometric view of the second carriage illustrated in FIG. 13.

Referring to FIGS. 13 and 14, the inspection system 20 may include a second carriage 62 that carries the first mirror 36. The second carriage 62 may be fixed in place with respect to the housing 22 and internal components of the inspection system 20 positioned within the housing 22. Alternatively, the second carriage 62 may be movable with respect to the housing 22 and internal components of the inspection system 20 positioned within the housing 22. According to one embodiment, the second carriage 62 is translatable so as to adjust the first distance D1 between the second mirror 40 and the first mirror 36.

According to one embodiment, the second carriage 62 has a front face 64 that faces the window 28. The front face 64 may have a recess 66 that is sized to receive the first mirror 36 such that the concave reflective surface 38 faces the window 28.

Figure 15:
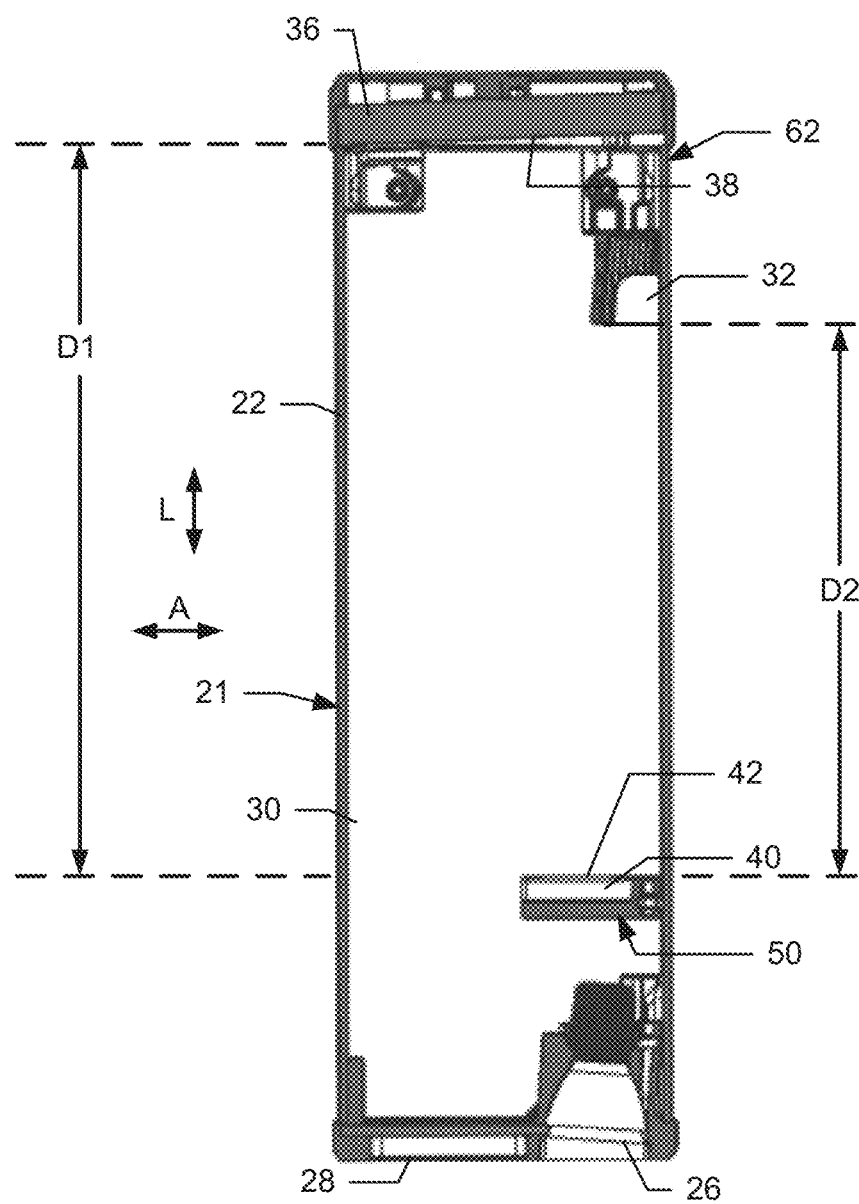
FIG. 15 is a top, plan view of internal components of the image capture apparatus illustrated in FIG. 3, according to one embodiment.

Referring to FIG. 15, the image sensor 32 may be carried by the second carriage 62 (as shown), by the first carriage 50, or supported by the housing 22 independent from both the first carriage 50 and the second carriage 62. Thus, according to one embodiment, adjusting the first distance D1, may also simultaneously adjust the second distance D2.

Figure 16:
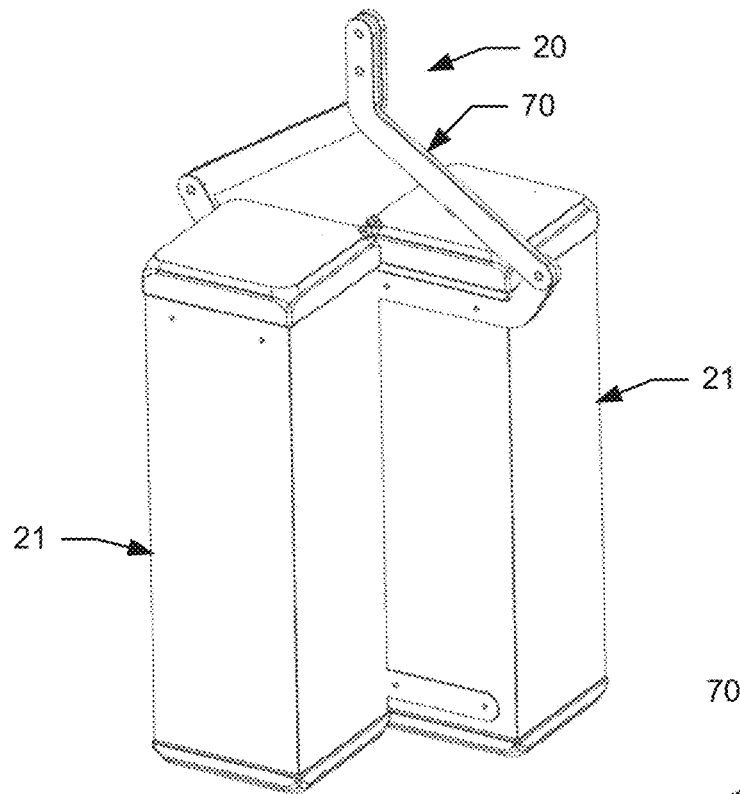
FIG. 16 is an isometric view of an inspection system assembly including a plurality of the image capture apparatuses illustrated in FIG. 1.
Figure 17:
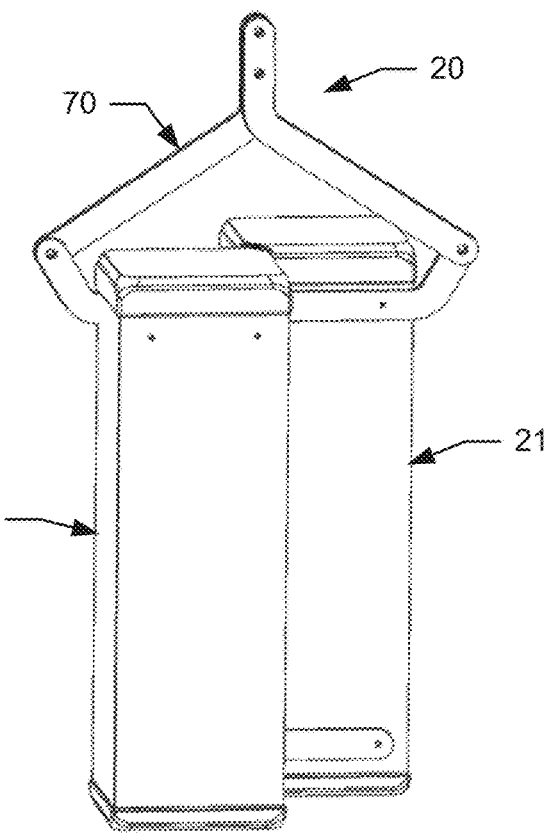
FIG. 17 is another isometric view of the inspection system assembly illustrated in FIG. 16.

Referring to FIGS. 16 and 17, the inspection system 20 may include one or more of the image capture apparatuses 21, for example two as shown in the illustrated embodiment. A plurality of the one or more image capture apparatuses 21 may be secured relative to one another, for example coupled together, in various configurations to achieve different outcomes. The plurality of image capture apparatuses 21 may be directly coupled together, for example by one or more fasteners that pass through both of the housings 22 of adjacent image capture apparatuses 21. According to another embodiment, the plurality of image capture apparatuses 21 may be indirectly coupled together, for example by a bracket 70, as shown in the illustrated embodiment. According to another embodiment, the plurality of image capture apparatuses 21 may be separated by a gap, for example such that each of the image capture apparatuses 21 is secured relative to the object 10 by a respective bracket (not shown).

Referring to FIGS. 4 to 7 and 16 to 17, according to one embodiment, adjacent ones of the image capture apparatuses 21 may be coupled together such that at least a portion of one or more of the first field of view 44 and the second field of view 46 of one of the adjacent image capture apparatuses 21 overlaps with at least a portion of one or more of the first field of view 44 and the second field of view 46 of another of the adjacent image capture apparatuses 21.

Overlapping fields of view may provide redundancy to compensate for a failure of one of the image capture apparatuses 21. Overlapping fields of view may provide quality control to ensure the image capture apparatuses 21 are operating properly. For example if a measurement of an area of the object 10 within the overlapping field of view is inconsistent between adjacent image capture apparatuses 21, it may indicate a problem with one of the adjacent image capture apparatuses 21.

According to one embodiment, adjacent ones of the image capture apparatuses 21 may be coupled together such that at least a portion of one or more of the first field of view 44 and the second field of view 46 of one of the adjacent image capture apparatuses 21 is discreet from, i.e. does not overlap with, at least a portion of one or more of the first field of view 44 and the second field of view 46 of another of the adjacent image capture apparatuses 21. Discreet fields of view may provide the ability for the inspection system 20 to capture an image of wider objects 10. Discreet fields of view may provide enhanced quality of images of objects 10 with uneven surfaces, such that a portion of an uneven surface is blocked from line of sight to one of the image capture apparatuses 21 in a first position, but not blocked from line of sight to another of the image capture apparatuses 21 in a second position.

Referring to FIGS. 1 to 17, one embodiment of a method of manufacturing the inspection system 20 may include providing the housing 22 having the window 28, locating at least one of the image sensor 32 in the housing 22, locating the first mirror 36 in the housing 22 such that the concave reflective surface 38 faces the window 28, and locating the second mirror 40 in the housing 22 such that the reflective surface 42 faces the concave reflective surface 38. The second mirror 40 located within the housing 22 such that the second mirror 40 is spaced from the first mirror 36 by the first distance D1, which is adjustable to position the second mirror 40 relative to the focal point of the first mirror 36. The first mirror 36 is positioned and oriented in the housing 22 to reflect the light 16 received via the window 28 of the housing 22 toward the second mirror 40, and the second mirror 40 is positioned and oriented in the housing 22 to reflect toward the at least one image sensor 32 the light 16 that was reflected toward the second mirror 40 by the first mirror 36.

According to one embodiment locating the first mirror 36 in the housing 22 includes locating a concave mirror in the second carriage 62. According to one embodiment, locating the second mirror 40 in the housing 22 includes locating a flat mirror in the first carriage 50. Locating the second mirror 40 in the first carriage 50 may include providing the first carriage 50 having the front face 56 that faces the window 28 and the back face 58 opposed across a thickness of the first carriage 50 from the front face 56.

The method of manufacturing may include adjusting the first distance D1 between the first mirror 36 and the second mirror 40. Adjusting the first distance D1 may include providing the threaded fastener 51 that threadedly engages the first carriage 50 and is rotatable to adjust the first distance D1 between the first mirror 36 and the second mirror 40. Adjusting the first distance D1 may further include rotating the threaded fastener 51 to thereby move the first carriage 50 and the second mirror 40 relative to the second carriage 62 and the first mirror 36. Adjusting at least one of the first distance D1 and the second distance D2 may include inserting an actuator through an opening, for example the access 54, in the housing 22.

Locating the at least one image sensor 32 in the housing 22 may include locating the at least one image sensor 32 such that at least a portion of the first field of view 44 encompasses at least a portion of the window 28 that is outside the second field of view 46. According to one embodiment, the method of manufacturing may further include providing at least one light emitter diode to the housing 22, the at least one light emitter diode positioned and oriented to emit the light 16 toward an external environment, for example including the object 10, in front of the window 28 of the housing 22. According to one embodiment, the method of manufacturing may further include communicatively coupling the at least one processor 17 to the at last one image sensor 32 to receive image data therefrom and to detect cuts in the object 10 appearing in images represented by the image data, and to determine one or more dimensions based at least in part on the detected cuts.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art.

Many of the methods described herein can be performed with variations. For example, many of the methods may include additional acts, omit some acts, and/or perform acts in a different order than as illustrated or described. The various embodiments described above can be combined to provide further embodiments.

U.S. Pat. Nos. 5,034,259; 5,135,597; 7,853,349; 7,886,642; 7,914,175; 7,993,019; 8,229,803; 8,346,631; 8,370,222; 9,505,072; and 9,827,643 and U.S. Patent Application Publication Nos. 2006/0053990; 2009/0076741; 2014/0238546; and 2014/0251499 are each incorporated herein by reference, in their entirety. Aspects of the embodiments can be modified, if necessary to employ concepts of the various patents and publications listed above to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An image capture apparatus comprising:
a housing having a window;
a first mirror located in the housing, the first mirror having a concave parabolic reflective surface, and the first mirror having a focal point at which parallel rays of light that enter the housing through the window and reflect off of the concave parabolic reflective surface intersect;
a second mirror located in the housing, the second mirror having a flat reflective surface, the second mirror positioned and oriented in the housing to reflect toward the focal point the parallel rays of light reflected by the first mirror; and
at least one image sensor located in the housing at the focal point,
wherein the second mirror is spaced from the first mirror by a first distance measured along a direction parallel to the parallel rays of light, the at least one image sensor is spaced from the second mirror by a second distance measured along the direction parallel to the parallel rays of light, and at least one of the first mirror, the second mirror, and the at least one image sensor is movable relative to the others of the first mirror, the second mirror, and the at least one image sensor such that at least one of the first distance and the second distance is adjustable, and
wherein the at least one image sensor is positioned within the housing such that the at least one image sensor has a direct line of sight through the window of the housing.

2. The image capture apparatus of claim 1, further comprising:
at least one source of flood illumination positioned to emit light toward an object such that a portion of the light reflects off of the object and towards the window.

3. The image capture apparatus of claim 2 wherein the source of flood illumination includes a light emitter diode (LED) carried by the housing.

4. The image capture apparatus of claim 1, further comprising:
a carriage that carries the second mirror, the carriage translatable with respect to the first mirror to adjust the distance between the second mirror and the first mirror.

5. The image capture apparatus of claim 4, further comprising:
a threaded fastener that threadedly engages the carriage and is rotatable to adjust the first distance.

6. The image capture apparatus of claim 5 wherein each one quarter turn of the threaded fastener adjusts the first distance by ten thousandths of an inch.

7. The image capture apparatus of claim 1, further comprising:
a carriage that carries the first mirror, the carriage translatable with respect to the second mirror to adjust the first distance.

8. The image capture apparatus of claim 1, further comprising:
a carriage that carries the first mirror and the at least one image sensor.

9. The image capture apparatus of claim 1 wherein the window includes a transparent pane, and the transparent pane, the first mirror and the second mirror are the only optics in an optical path that extends from an exterior of the housing to the at least one image sensor.

10. The image capture apparatus of claim 1, further comprising:
at least one processor communicatively coupled to the at last one image sensor to receive image data therefrom and operable to detect cuts appearing in images represented by the image data, and to determine one or more dimensions based at least in part of the detected cuts.

11. The image capture apparatus of claim 1 wherein the housing is a first housing, the window is a first window, the concave parabolic surface is a first concave parabolic surface, the focal point is a first focal point, the flat reflective surface is a first flat reflective surface, the at least one image sensor is at least one first image sensor, and the image capture apparatus further comprises:
a second housing having a second window;
a third mirror located in the second housing, the third mirror having a second concave parabolic reflective surface, and the third mirror having a second focal point at which parallel rays of light that enter the second housing through the second window and reflect off of the second concave parabolic reflective surface intersect;
a fourth mirror located in the second housing, the fourth mirror having a second flat reflective surface, the fourth mirror positioned and oriented in the second housing to reflect toward the second focal point the parallel rays of light reflected by the third mirror; and
at least one second image sensor located in the second housing at the second focal point,
wherein the fourth mirror is spaced from the third mirror by a third distance measured along the direction parallel to the parallel rays of light, the at least one second image sensor is spaced from the fourth mirror by a fourth distance measured along the direction parallel to the parallel rays of light, and at least one of the third mirror, the fourth mirror, and the at least one second image sensor is movable relative to the others of the third mirror, the fourth mirror, and the at least one image second sensor such that at least one of the third distance and the fourth distance is adjustable.

12. The image capture apparatus of claim 11, further comprising:
a bracket supporting both the first housing and the second housing such that the first housing and the second housing are fixed relative to one another.

13. A method of manufacturing a sawing inspection system, the method comprising:
providing a housing having a window;
locating a first mirror in the housing, the first mirror having a concave parabolic reflective surface, and the first mirror having a focal point at which parallel rays of light that enter the housing through the window and reflect off of the concave parabolic reflective surface intersect;
locating a second mirror in the housing such that a flat reflective surface of the second mirror is positioned and oriented to reflect toward the focal point the parallel rays of light reflected by the first mirror, the second mirror spaced from the first mirror by a first distance that is measured along a direction parallel to the parallel rays of light; and
locating at least one image sensor in the housing such that the at least one image sensor is spaced from the first mirror by a second distance that is measured along the direction parallel to the parallel rays of light;
adjusting at least one of the first distance and the second distance to position the at least one image sensor at the focal point, wherein when the at least one image sensor is at the focal point the at least one image sensor has a direct line of sight through the window of the housing.

14. The method of claim 13 wherein adjusting at least one of the first distance and the second distance includes inserting an actuator through an opening in the housing.

15. The method of claim 14, further comprising:
activating a source of illumination thereby producing light including the parallel rays of light.

16. The method of claim 15, further comprising:
blocking the opening with the source of illumination by coupling the source of illumination to the housing.

17. The method of claim 13, further comprising:
providing a threaded fastener; and
rotating the threaded fastener to adjust at least one of the first distance and the second distance.

18. The method of claim 13, further comprising:
communicatively coupling at least one processor to the at last one image sensor to receive image data therefrom and to detect cuts appearing in images represented by the image data, and to determine one or more dimensions based at least in part of the detected cuts.

19. A method of measuring at least one dimension of a cant that has been sawn into at least one board, the method comprising:
activating a source of illumination to produce light which reflects off of the cant;
positioning an image capture apparatus such that parallel rays of light from the light that has reflected off of the cant passes through a window of a housing of the image capture apparatus, then reflects off of a concave parabolic reflective surface of a first mirror of the image capture apparatus, and then is received by an image sensor of the image capture apparatus positioned at a focal point of the first mirror at which the parallel rays of light intersect;
simultaneously capturing a first image of the object and a second image of the object, the first image generated based on the parallel rays of light that reflected off of the first mirror to the image sensor, and the second image based on light reflected off of the cant, through the window, and directly to the image sensor without reflecting off the first mirror.

20. The method of claim 19 wherein positioning the image capture apparatus includes positioning a second mirror of the image capture apparatus such that the parallel rays of light reflect off of the first mirror, then reflect off of a flat reflective surface of the second mirror, and then intersect at the focal point.

21. The method of claim 19 wherein at least a portion of the first image and at least a portion of the second image are of the same portion of the object.

22. The method of claim 19, further comprising:
analyzing the first image to detect a first cut in the cant and a second cut in the cant; and
computing a parallax-corrected distance from the first cut to the second cut based on the first image, the parallax-corrected distance measured along a first direction.

23. The method of claim 22, further comprising:
analyzing the second image to detect the first cut in the cant and the second cut in the cant; and
computing a non-parallax corrected distance from the first cut to the second cut based on the second image, the non-parallax corrected distance measured along the first direction.

24. The method of claim 23, further comprising:
comparing the parallax-corrected distance to the non-parallax corrected distance to compute a dimension of the cant measured in a second direction, the second direction perpendicular to the first direction.

25. The method of claim 24, further comprising:
moving the cant relative to the image capture apparatus along a third direction perpendicular to both the first direction and the second direction.

26. The method of claim 25 wherein capturing the first image of the object and the second image of the object is performed simultaneously with moving the cant relative to the image capture apparatus along the third direction.

* * * * *